US012638106B2

(12) United States Patent (10) Patent No.: US 12,638,106 B2
Atakan (45) Date of Patent: May 26, 2026

(54) TUBE SET SEAL ASSEMBLY

(71) Applicant: Keymed (Medical & Industrial Equipment) Limited, Southend-on-Sea (GB)

(72) Inventor: Nevzat Atakan, Southend-on-Sea (GB)

(73) Assignee: Keymed (Medical & Industrial Equipment) Limited, Southend-on-Sea (GB)

( * ) Notice: Subject to any disclaimer, the term of this patent is extended or adjusted under 35 U.S.C. 154(b) by 857 days.

(21) Appl. No.: 17/899,748

(22) Filed: Aug. 31, 2022

(65) Prior Publication Data

US 2023/0110822 A1 Apr. 13, 2023

Related U.S. Application Data

(60) Provisional application No. 63/255,091, filed on Oct. 13, 2021.

(51) Int. Cl.
*A61M 39/10* (2006.01)
*B65D 39/12* (2006.01)
*F16L 5/14* (2006.01)

(52) U.S. Cl.
CPC ............... *F16L 5/14* (2013.01); *B65D 39/12* (2013.01); *A61M 39/10* (2013.01)

(58) Field of Classification Search
CPC ........ A61M 1/60; A61M 1/69; A61M 39/105; A61M 39/12; A61M 2039/1077; A61J 1/1481; B65D 39/025; B65D 39/12; B65D 47/06; B65D 47/12; B65D 47/121; B65D 47/123; B65D 47/141; B65D 47/143; B65D 2539/003; B65D 2539/006; B65D 2547/06; F61L 5/10; F61L 5/12;

F61L 5/14; A61B 1/00119; A61B 17/3423; A61B 2017/3419; A61B 2017/3425; A61B 2017/3427; A61B 2017/3429; A61B 2017/3445; A61B 2017/3486
See application file for complete search history.

(56) References Cited

U.S. PATENT DOCUMENTS 5,002,557 A * 3/1991 Hasson ................... A61B 17/34
604/174
2011/0315147 A1* 12/2011 Wood ................ A61M 16/0463
128/207.15

FOREIGN PATENT DOCUMENTS

GB 2 548 850 A 10/2017
JP 2002-087407 A 3/2002

OTHER PUBLICATIONS

"Counterbore vs Countersink: Understanding the Differences" <<https://leadrp.net/blog/counterbore-vs-countersink-understanding-the-differences/>> (Year: 2023).*
Great Britain Search Report dated Mar. 1, 2022 received in GB2114680.8.

* cited by examiner

*Primary Examiner* — Kami A Bosworth
(74) *Attorney, Agent, or Firm* — Scully, Scott, Murphy & Presser, P.C.

(57) ABSTRACT

A tube set seal assembly including: a body configured for insertion into an opening of a container, a plurality of passages extending through the body, and an inflatable annular seal provided on the body. Wherein the body comprises an inflation channel in communication with the seal for supply of gas to the seal to cause the seal to inflate.

11 Claims, 8 Drawing Sheets

TUBE SET SEAL ASSEMBLY

CROSS-REFERENCE TO RELATED APPLICATION

The present application is based upon and claims the benefit of priority from U.S. Provisional Application No. 63/255,091 filed on Oct. 13, 2021, the entire contents of which is incorporated herein by reference.

BACKGROUND

Field

The present disclosure relates to a seal assembly for a medical tube set used for irrigation and insufflation during endoscopic procedures.

Prior Art

During endoscopic procedures it is usual to provide a supply of liquid, such as sterile water, and gas, such as air or $CO_2$, to an endoscope. Liquid is used to rinse the endoscope lens and to irrigate the site under inspection. Gas is used to insufflate the body cavity under inspection. Liquid and gas are normally supplied by a tube set attached to a bottle containing liquid and pressurized with gas from a gas supply.

A conventional tube set comprises a bottle cap with an internal thread for connection to the external thread on the neck of a bottle. A number of tubes pass through the cap into the bottle for conveying liquid and gas. It is necessary for the cap to fit the bottle with a gas-tight seal but since various types of bottles are available with different shapes and sizes, a single tube set cap may not fit and provide a satisfactory seal with all the types of bottles commonly in use.

SUMMARY

Accordingly, a tube set seal assembly is provided. The tube set seal assembly comprising a body configured for insertion into an opening of a container, a plurality of passages extending through the body, an inflatable annular seal provided on the body, and an inflation channel in the body in communication with the seal for supply of gas to the seal to cause it to inflate.

The tube set seal assembly can be used with a variety of containers with openings of different sizes while ensuring an effective seal against the container opening.

The seal can comprise a hollow annular member with an outer annular surface having an outer diameter and an inner annular surface having an inner diameter, wherein the seal is configured such that inflation causes the outer annular surface to extend radially away from the inner annular surface to increase the outer diameter.

The seal can comprise an inflation port on the inner annular surface which communicates with the inflation channel in the body.

The body can further comprise an annular groove in which the seal is seated, and the inflation channel can extend between one of the passages through the body and the annular groove.

The seal can be shaped so that virtually all the expansion occurs in a radially outward direction, so that the outer annular surface moves radially outwardly away from the inner annular surface.

The body can be cylindrical and can comprise first and second ends and a longitudinal axis, the passages can extend axially through the body between the first and second ends and each passage can comprise a counterbore at the first end and at the second end, each bore can be configured to receive the end of a tube.

The body can further comprise a stop member at the first end of the body configured to limit the insertion of the body into an opening of a container and the seal can be provided close to the second end of the body.

The stop member can comprise an annular member on the body having an outer diameter which is greater than the outer diameter of the body.

In another embodiment, the stop member can further comprise a wall depending from the stop member and surrounding the body, and at least one ridge projecting inwardly from an interior surface of the wall and configured to engage with an exterior thread formed on the opening of a container. The wall can be generally cylindrical and can further comprise at least one axially extending slot.

In one embodiment, the body can comprise first and second ends and a longitudinal axis, the passages can extend axially through the body between the first and second ends, and wherein the inflation channel can communicate between one of the passages and the seal.

In another embodiment, the body can comprise first and second ends and a longitudinal axis, the passages can extend axially through the body between the first and second ends, and wherein the inflation channel can extend from the first end to the seal and does not extend to the second end.

Also provided is a tube set comprising a tube set seal assembly as described above in combination with a plurality of tubes, wherein each end of each passage through the body is attached in communication with a respective tube.

Still further provides is a method of fitting a tube set in an opening of a container, the method comprising: providing a body configured for insertion into an opening of a container, the body comprising first and second ends and a plurality of passages extending through the body, an inflatable annular seal provided on the body, and an inflation channel in the body in communication with the seal; securing a tube to each passage at the first end and at the second end of the body; positioning the body in the opening of a container with the tubes secured to the first end of the body extending out of the container and the tubes secured to the second end of the body extending into the container; and supplying gas through the inflation channel to cause the seal to inflate and seal against a surface of the opening.

The method can further comprise providing a stop member at the first end of the body to limit insertion of the body into the opening.

BRIEF DESCRIPTION OF THE DRAWINGS

The embodiments will now be described in detail, by way of example only, with reference to the accompanying drawings in which.

DETAILED DESCRIPTION

Figure 1:
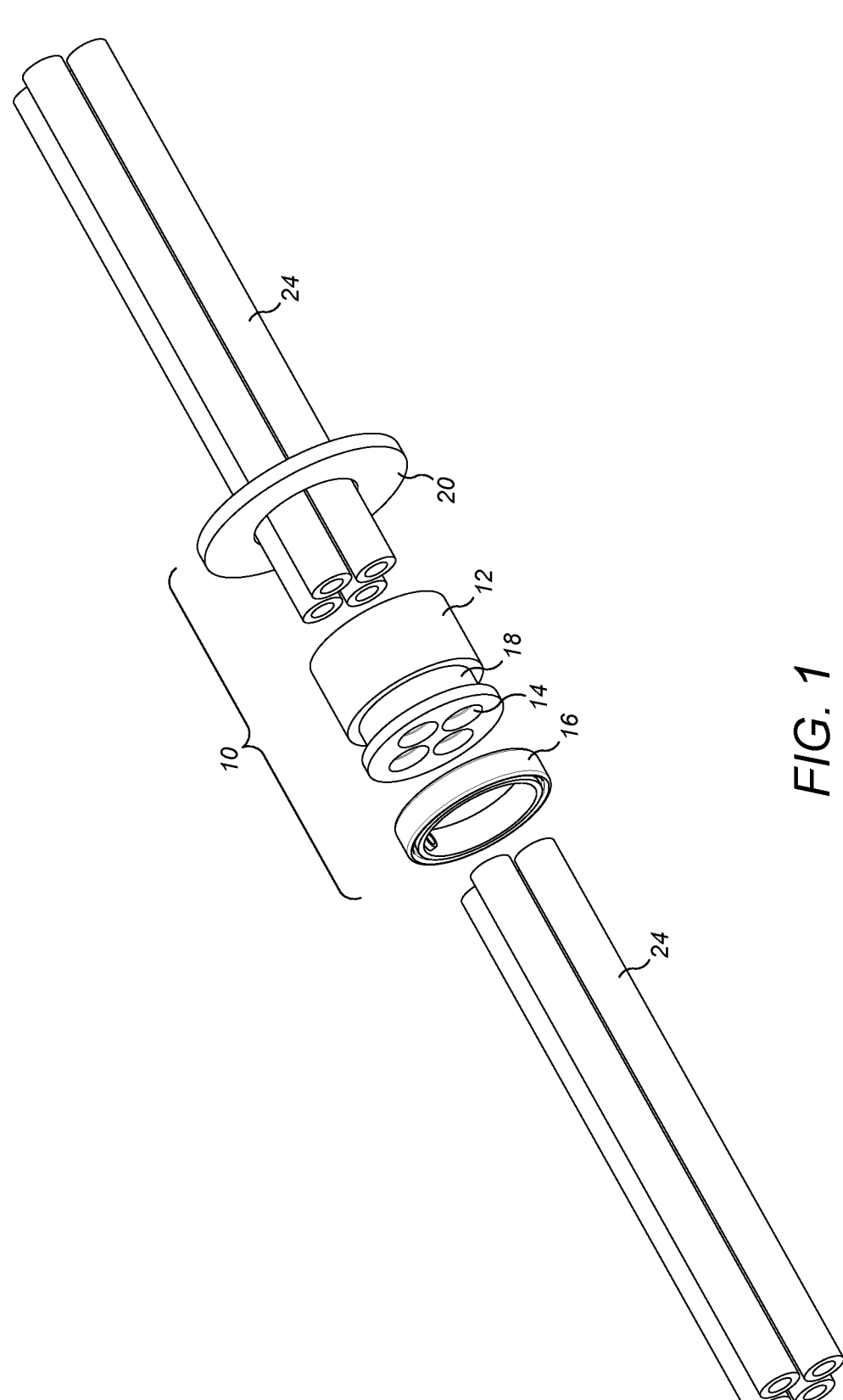
FIG. 1 illustrates an exploded perspective view of a tube seal assembly.
Figure 2:
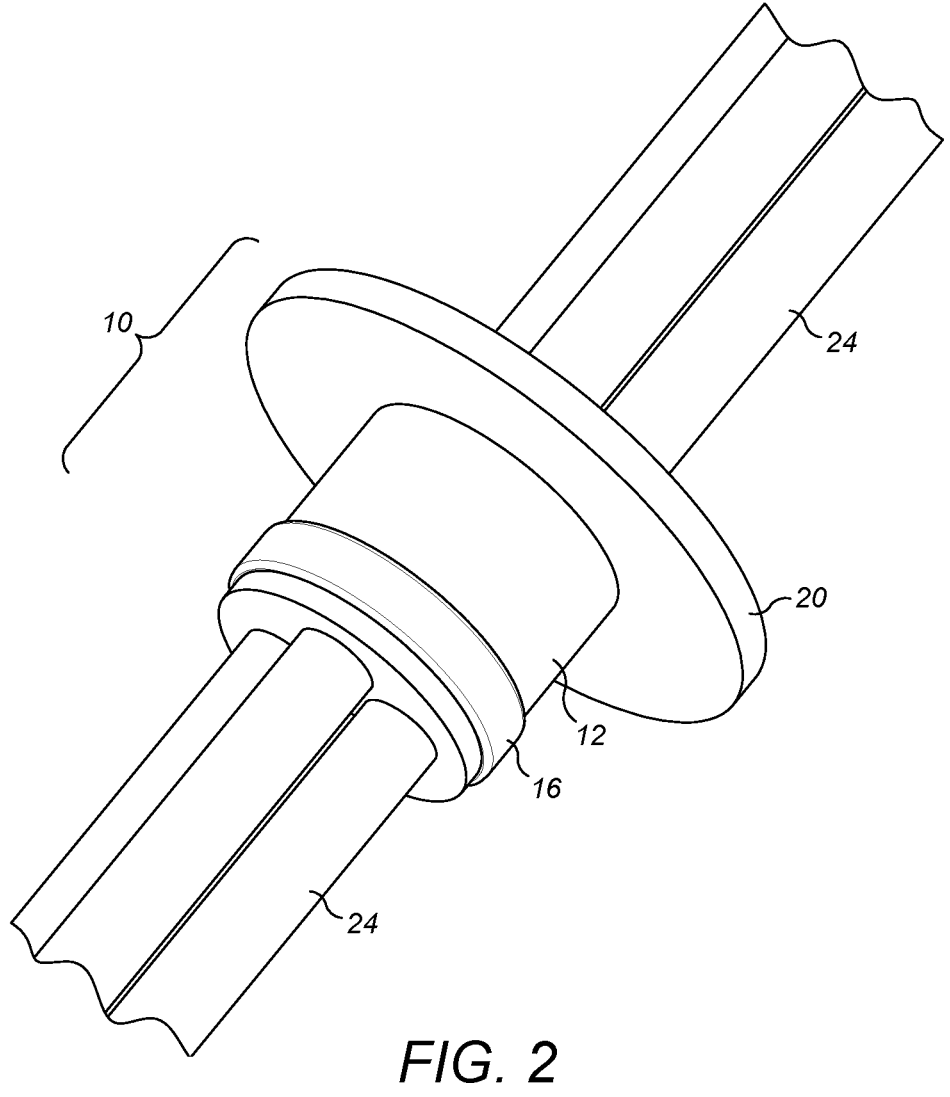
FIG. 2 illustrates an assembled view of the tube set seal assembly of FIG. 1.

As shown in FIGS. 1 and 2, a tube set seal assembly 10 in accordance with one embodiment comprises a body 12. This is intended to fit within an opening of a container, e.g., in the neck of a bottle. Therefore, the body 12 is typically a generally cylindrical body with a diameter slightly smaller than the internal diameter of a typical range of bottle necks.

Figure 3:
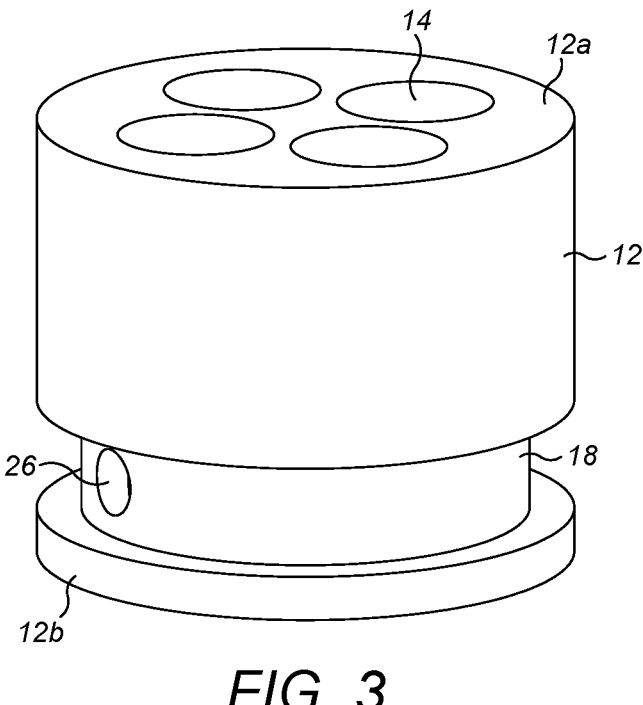
FIG. 3 illustrates a perspective view of the main body of the tube set seal assembly.
Figure 4:
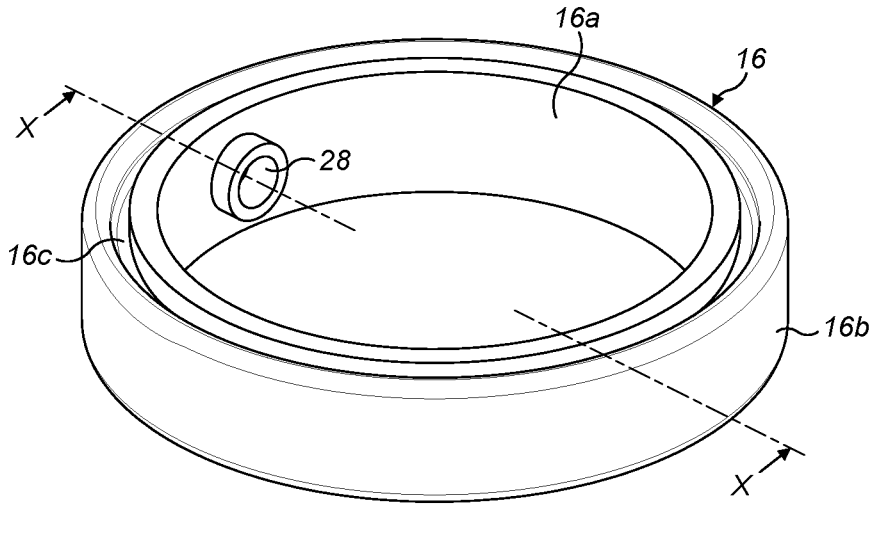
FIG. 4 illustrates a perspective view of the seal member.

The body 12 has first and second ends 12a, 12b as shown in FIG. 3, and at least one passage 14 extending axially through the body 12 between the first and second ends 12a, 12b. In this example, four passages are provided. The passages 14 can be parallel and equally spaced. In use, a tube 24 is attached to the body 12 at each end of each passage 14 to create a tube set.

An annular seal 16 is provided around the body 12. The seal 16 can be located in an annular groove 18 formed in the body 12, close to the second, lower end 12b.

A stop member 20 can be provided on the opposite, upper end 12a of the body 12 and extends out radially to a diameter greater than that of an opening, such as a bottle neck, into which the body 12 is to be inserted.

Figure 7:
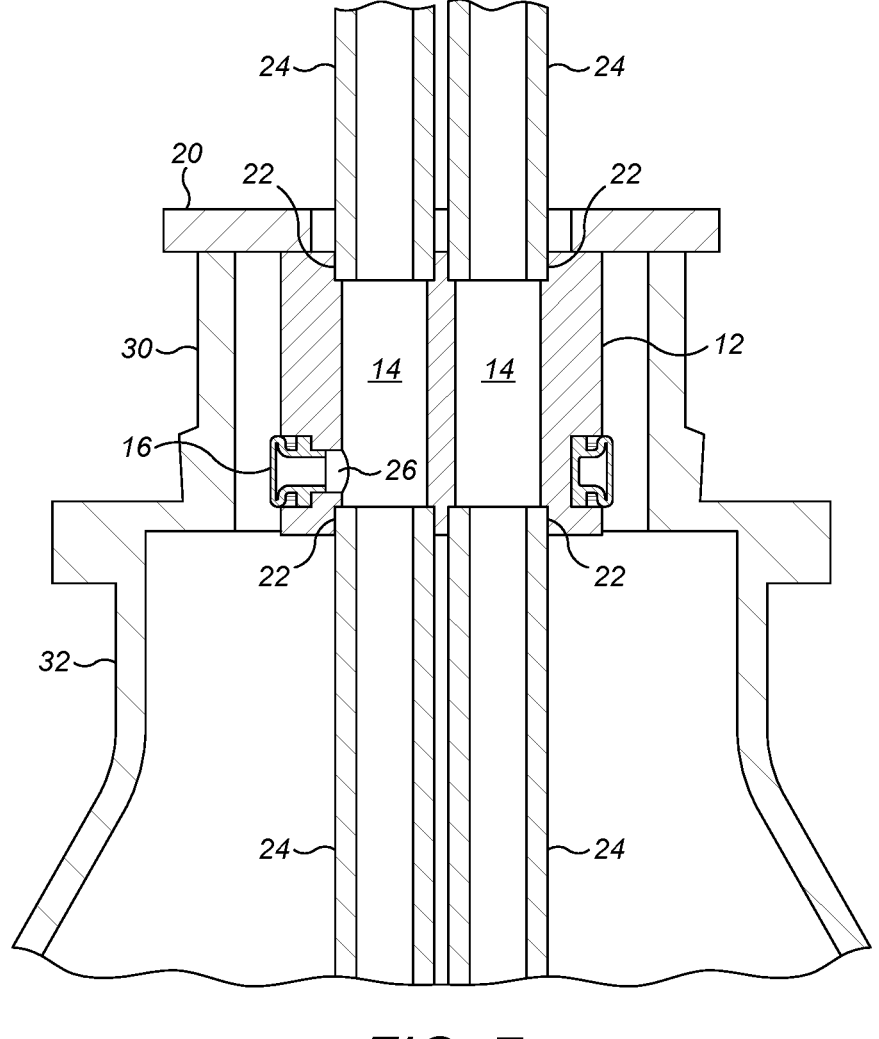
FIG. 7 illustrates a cross-section of the assembly located in the neck of a bottle, in an uninflated state.
Figure 8:
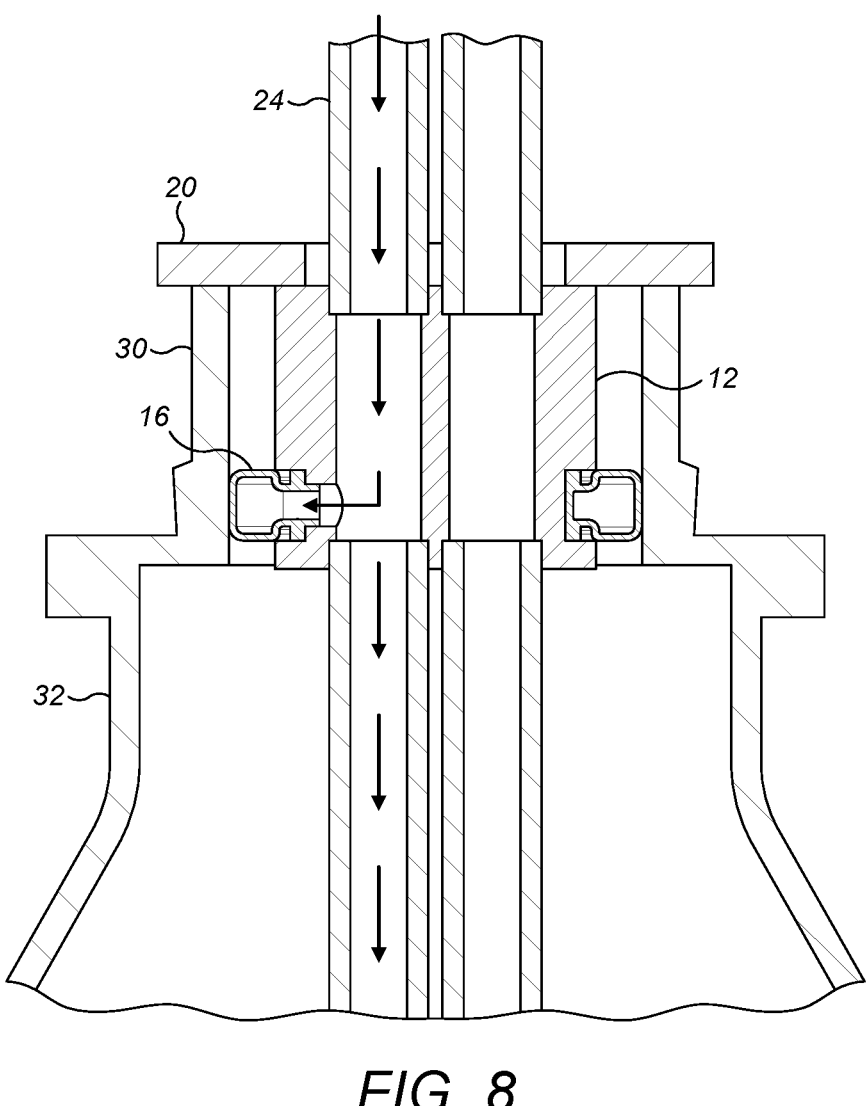
FIG. 8 illustrates the assembly of FIG. 7 in an inflated state.

As shown in FIGS. 7 and 8, the axial passages 14 through the body 12 can have a counterbore 22 of larger diameter formed at each end, to receive the end of a respective tube 24. Each tube 24 can be bonded in place in a respective bore 22, to create the tube set. The diameter of each passage 14 can be slightly larger than the inner diameter of the tube 24. The diameter of each counterbore 22 is substantially the same as the outer diameter of the tube 24. Accordingly, the end of each tube 24 can be located within a counterbore 22 for secure and gas-tight attachment to the body 12.

A radially extending inflation channel 26 extends through the body 12 between one of the axial passages 14 and the annular groove 18.

The body 12 can be formed from a rigid, inert polymer such as ABS (acrylonitrile butadiene styrene) or PC-ABS (polycarbonate/acrylonitrile butadiene styrene). It may be manufactured by an extrusion process, followed by machining to create to the annular groove 18 and the radial inflation channel 26, or a moulding process such as injection moulding, with sliding cores on the mould. However, other materials and manufacturing processes may also be used.

The stop member 20 in this example is an annular collar provided on the body 12. This may be a separate item which is joined to the body 12 or it may be formed integrally with the body 12. An annular stop member 20 could be replaced by a number of radially extending projections spaced around the body 12. The stop member 20 has an outer diameter larger than the diameter of a container opening into which the body 12 is to be inserted. In use, the stop member 20 will engage against the upper edge of such an opening, e.g., a bottle neck, to limit how far into the bottle the body 12 can be inserted. When the stop member 20 is a continuous annulus, it also helps to close the container opening even before the seal 16 is fully engaged (as described below).

If the stop member 20 is a separate item, it can be made from the same material as the body 12 and can be formed by any convenient process such as laser cutting, stamping or extrusion and subsequently bonded to the body 12.

The seal 16 comprises a hollow annular member formed of resilient, flexible material, for example a polymer such as silicone, EPDM (ethylene propylene diene monomer) or a fluoropolymer elastomer and synthetic rubber compound such as Viton™. The seal 16 has an inner annular wall 16a and an outer annular wall 16b. A port 28 is formed on the inner wall 16a of the annulus, communicating with the hollow interior of the seal 16.

Figure 5:
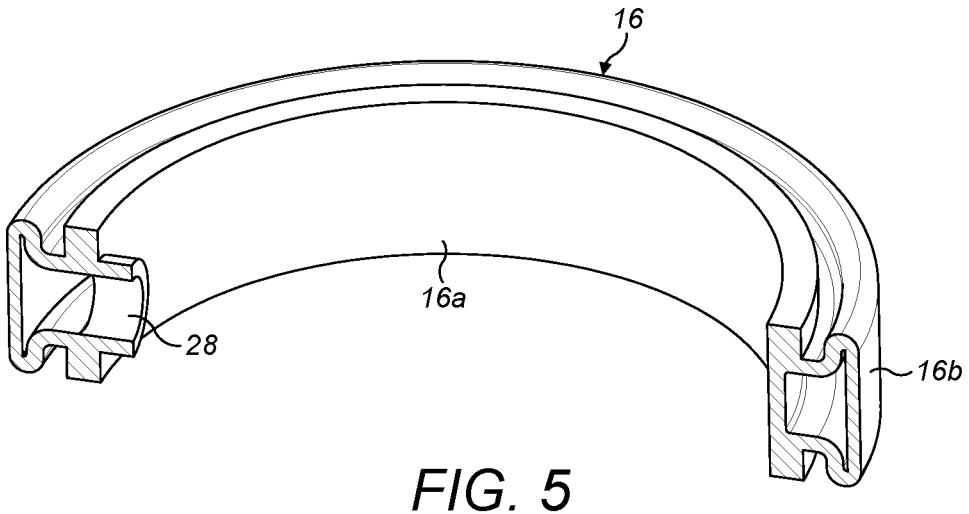
FIG. 5 illustrates a cross-section of the seal member of FIG. 4 along the line XX, in an uninflated state.
Figure 6:
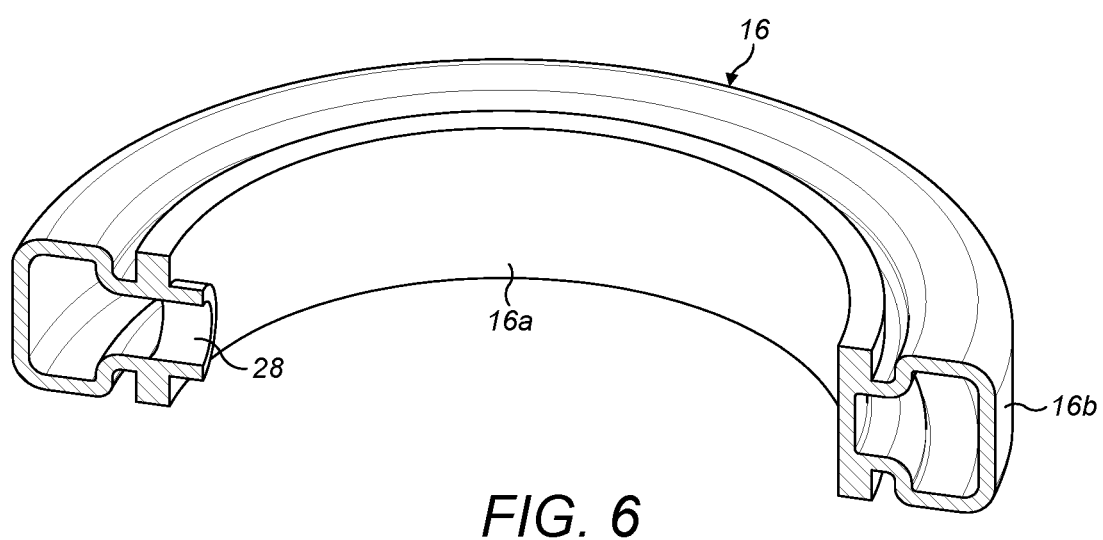
FIG. 6 illustrates a cross-section of the seal of FIG. 4 along the line XX, in an inflated state.

The seal 16 locates in the annular groove 18 with the inner annular wall 16a contacting the body 12. The port 28 is seated within the inflation channel 26 so that the interior of the seal 16 is in communication with the relevant axial passage 14 in the body 12. The seal 16 has a cross-sectional shape which is formed to allow for radial expansion of the seal 16 when it is inflated, as shown in FIGS. 5 and 6. In the deflated state, the outer annular wall 16b of the seal 16 has an outer diameter which is less than the inner diameter of a typical container opening/bottle neck. Once inflated, the outer diameter of the outer annular wall 16b is greater than the inner diameter of a typical container opening/bottle neck. The seal 16 can be shaped so that virtually all the expansion occurs in a radially outward direction, so that the outer annular wall 16b moves outwardly away from the inner annular wall 16a. For example, the inner and outer annular walls 16a, 16b may be joined by a flexible section 16c which expands when the seal 16 is inflated. The inner annular wall 16a remains seated within the groove 18, with the port 28 seated within the inflation channel 26, to avoid any gaps which would permit gas leakage.

In use, tubes 24 are secured to the body 12 at the first and second ends 12a, 12b and in communication with the passages 14 to create a tube set, and the seal 16 is initially in a deflated state. As shown in FIG. 7, the body 12 is inserted into a container opening, such as the neck 30 of a bottle 32, until the stop member 20 (if present) contacts the upper edge of the bottle neck 30. Gas, such as air or $CO_2$, is passed through the relevant axial passage 14 which communicates with the inflation channel 26. As shown by the arrows in FIG. 8, some gas passes into the seal 16 via the inflation channel 26 and the inflation port 28 and causes the seal 16 to inflate. The seal 16 expands radially and the outer annular wall 16b presses against the inner surface of the bottle neck 30 as shown in FIG. 8. Thus, the tube set seal assembly 10 becomes sealed in position in the bottle neck 30 and the interior of the bottle 32 can be pressurised by further gas passing through the tube 24 which does not enter the seal 16. Liquid and gas can be conveyed out of the bottle 32 via the remaining tubes 24 and axial passages 14.

Figure 9:
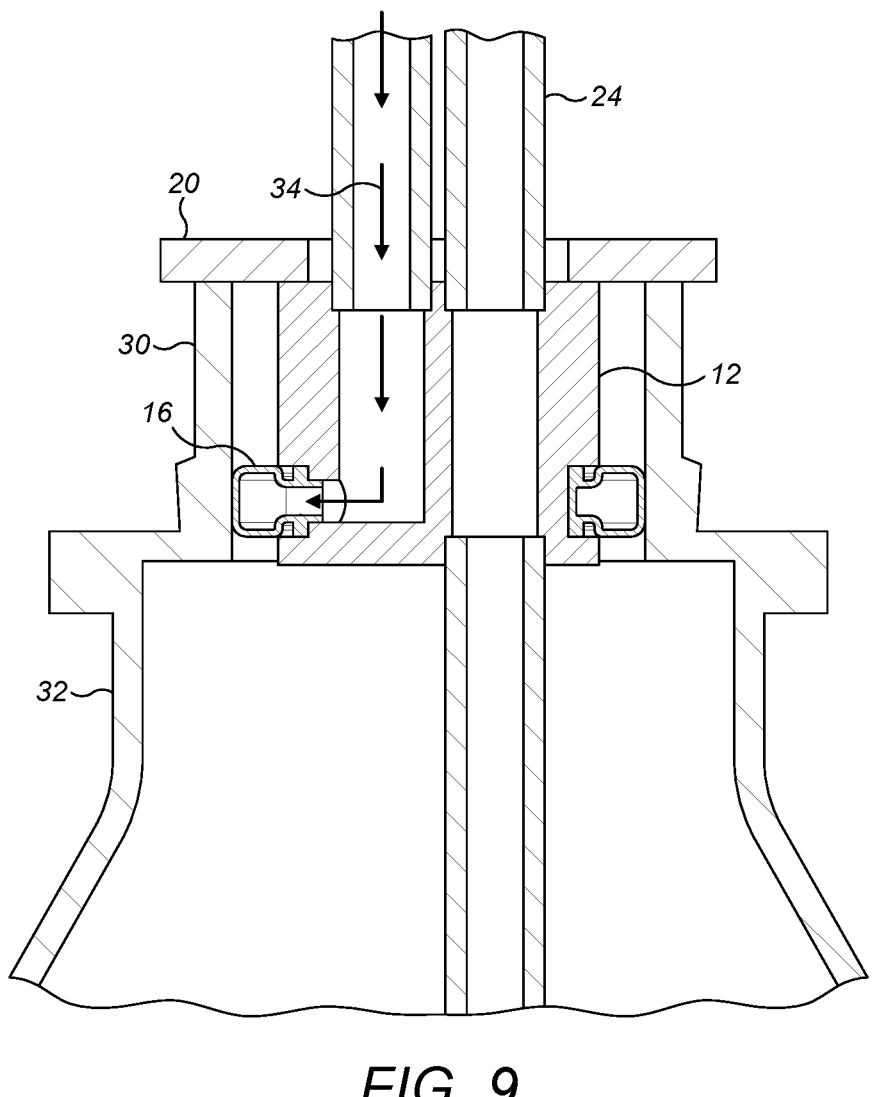
FIG. 9 illustrates a cross section of an alternative embodiment of tube set seal assembly, located in the neck of a bottle, in an inflated state.

In an alternative configuration, as shown in FIG. 9, a dedicated inflation channel 34 may be provided which extends from the first end 12a of the body 12 to communicate only with the inflation port 28 of the seal 16 and does not pass all the way through the body 12 to the second end 12b to communicate with the interior of a bottle 32. In this way, gas can be supplied directly into to the seal 16 without affecting other flow of gas into the bottle.

Figure 10:
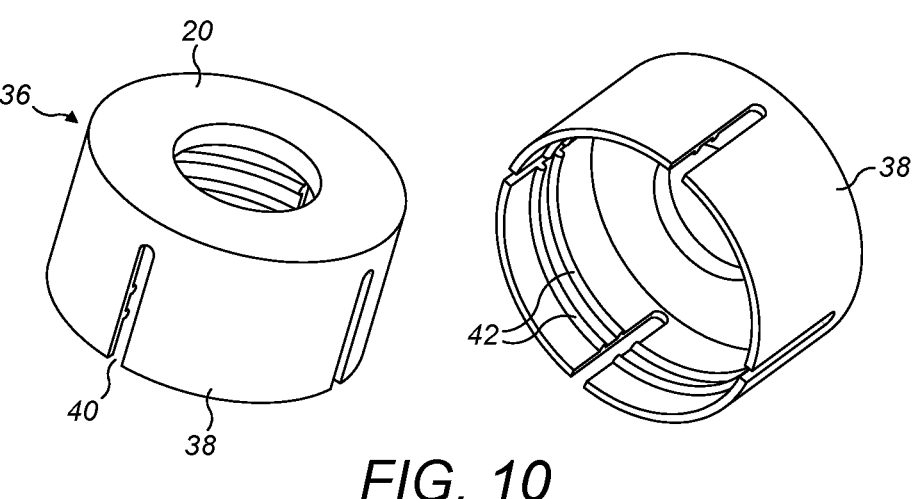
FIG. 10 illustrates upper and lower perspective views of a retention feature of another embodiment.
Figure 11:
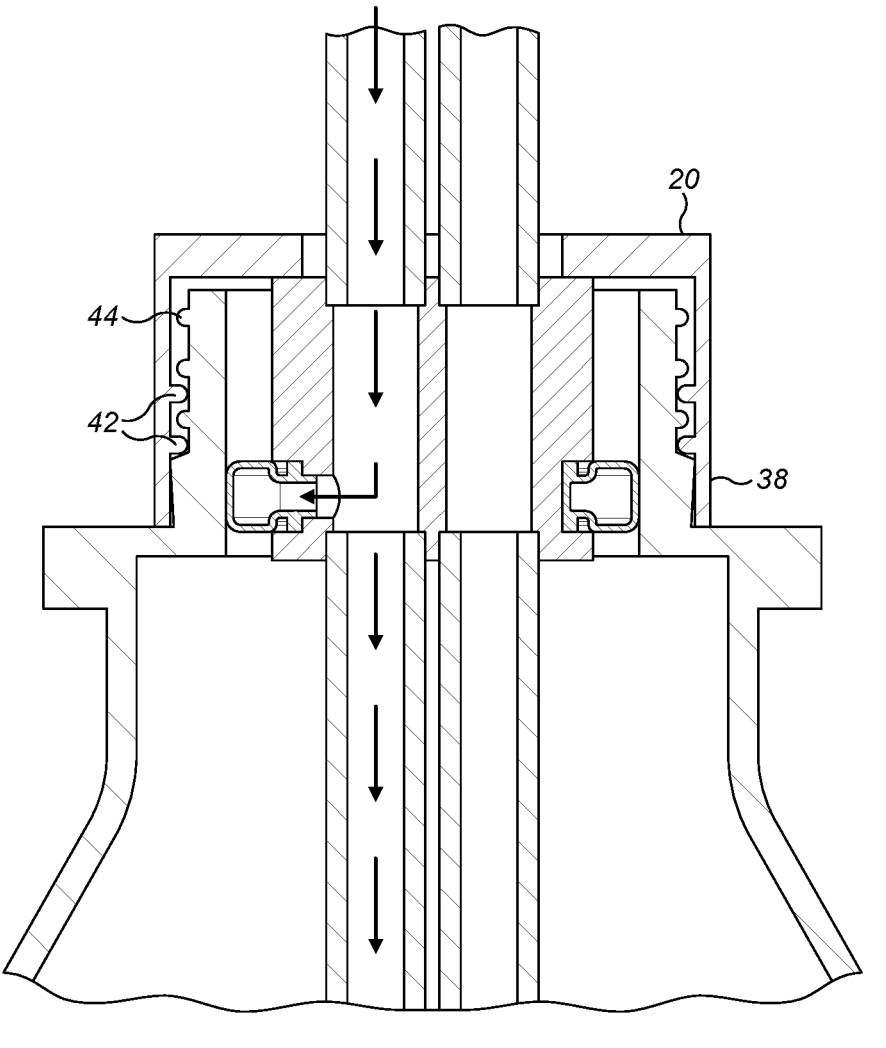
FIG. 11 illustrates a cross-section similar to FIG. 8, showing the retention feature of FIG. 10 in use.

Another embodiment is illustrated in FIGS. 10 and 11. In this embodiment, an additional retention feature 36 is provided to prevent the seal assembly 10 being pushed out of a container opening when the interior of the container is pressurised. In this embodiment, the stop member 20 is in the form of an annular ring as shown for example in FIGS. 1 and 2. However, the stop member 20 is also provided with a wall 38 depending downwardly from the outer perimeter of the ring. The wall 38 surrounds the body 12 but is spaced from it. The wall 38 is generally cylindrical and can include at least one axial slot 40 extending at least part of the way from the lower edge of the wall 38 towards the stop member 20. In this case, four equi-spaced slots 40 are provided, dividing the wall 38 into four arcuate segments. The interior surface of the wall 40 is formed with at least one, and in this case two, inwardly projecting annular ridges 42.

The stop member 20 and wall 38 are dimensioned to fit over the exterior of a bottle neck 30 as shown in FIG. 11. The body 12 and seal 16 are fitted within the bottle neck 30 as described above. The ridges 42 on the interior of the wall 38 engage with the external threads 44 on the bottle neck 30. The axial slots 40 allow some flexing of the wall 38 to facilitate fitting it over a bottle neck 30, and subsequent removal when required. The ridges 42 cooperate with the threads 44 to retain the seal assembly 10 in place within the bottle neck 30, even if the interior of the bottle 32 is pressurised by the supply of gas.

The retention feature 36 may be provided in conjunction with either embodiment above, that is the assembly of FIGS. 1-8 or that of FIG. 9.

Thus, a seal assembly is provided that allows a tube set to be effectively sealed in a variety of different container openings. It does not require a screw thread of exact dimensions to match that of a container opening.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A tube set seal assembly comprising:
   a body configured for insertion into an opening of a container, a plurality of passages extending through the body, and
   an inflatable annular seal provided on the body,
   wherein the body comprises an inflation channel in communication with the seal for supply of gas to the seal to cause the seal to inflate,
   wherein the body is cylindrical and comprises first and second ends and a longitudinal axis, the plurality of passages extend axially through the body between the first and second ends and each of the plurality of passages comprise a counterbore at the first end and at the second end, and each counterbore is configured to receive an end of a tube.

2. A tube set seal assembly as claimed in claim 1, wherein the seal comprises a hollow annular member with an outer annular surface having an outer diameter and an inner annular surface having an inner diameter, wherein the seal is configured such that inflation causes the outer annular surface to extend radially away from the inner annular surface to increase the outer diameter.

3. A tube set seal assembly as claimed in claim 2, wherein the seal comprises an inflation port on the inner annular surface which communicates with the inflation channel of the body.

4. A tube set seal assembly as claimed in claim 3, wherein the body further comprises an annular groove in which the seal is seated, and the inflation channel extends between one of the plurality of passages through the body and the annular groove.

5. A tube set seal assembly as claimed in claim 4, wherein the seal is shaped so that substantially all expansion occurs in a radially outward direction, so that the outer annular surface moves radially outwardly away from the inner annular surface.

6. A tube set seal assembly as claimed in claim 1, wherein the body further comprises a stop member at the first end of the body, the stop member being configured to limit insertion of the body into an opening of a container and the seal is provided adjacent to the second end of the body.

7. A tube set seal assembly as claimed in claim 6, wherein the stop member comprises an annular member having an outer diameter which is greater than an outer diameter of the body.

8. A tube set seal assembly as claimed in claim 7, wherein the stop member further comprises a wall extending from the annular member and surrounding the body, wherein at least one ridge projects inwardly from the wall and is configured to engage with an exterior thread formed on an opening of a container.

9. A tube set seal assembly as claimed in claim 8, wherein the wall is cylindrical and further comprises at least one axially extending slot.

10. The phrase "wherein the body comprises first and second ends and a longitudinal axis, wherein the plurality of passages extend axially through the body between the first and second ends, and" on lines 2-3 has been deleted since these features are now recited in claim 1.

11. A tube set comprising:
    the tube set seal assembly as claimed in claim 1; and
    a plurality of tubes, wherein each of the plurality of passages has a proximal end and a distal end, and wherein each proximal end and each distal end of each of the plurality of passages is attached in communication with a respective tube of the plurality of tubes.

\* \* \* \* \*